United States Patent

Sloan

(10) Patent No.: US 6,484,724 B1
(45) Date of Patent: Nov. 26, 2002

(54) UNIVERSAL RESPIRATORY DEVICE COUPLER

(76) Inventor: Ian Alexander Sloan, 10 Campbell Crescent, Toronto, Ontario (CA), M2P 1P2

(*) Notice: Subject to any disclaimer, the term of this patent is extended or adjusted under 35 U.S.C. 154(b) by 18 days.

(21) Appl. No.: 09/630,241

(22) Filed: Jul. 31, 2000

(51) Int. Cl.$^7$ .............................................. A61M 16/00
(52) U.S. Cl. ............................ 128/207.17; 128/202.27
(58) Field of Search .................... 128/207.14–207.18, 128/200.26, 911, 912, DIG. 26, 204.18, 202.27, 207.11, 206.27, 206.29; D24/129; 285/331, 272, 921; 604/905

(56) References Cited

U.S. PATENT DOCUMENTS

| | | | | |
|---|---|---|---|---|
| 3,388,705 A | * | 6/1968 | Grosshandler | 128/351 |
| 3,707,301 A | * | 12/1972 | Rauls | 285/9 R |
| D237,552 S | * | 11/1975 | Willmott | D24/129 |
| 4,369,911 A | * | 1/1983 | Blumenberg | 228/173 |
| 4,557,261 A | | 12/1985 | Rugheimer | 128/202.27 |
| 4,588,214 A | | 5/1986 | Guest | 285/323 |
| 4,589,684 A | * | 5/1986 | Nowacki et al. | 285/319 |
| 4,621,634 A | * | 11/1986 | Nowacki et al. | 128/204.18 |
| 4,774,940 A | * | 10/1988 | Linder | 128/204.18 |
| 4,827,921 A | * | 5/1989 | Rugheimer | 128/202.27 |
| 4,838,255 A | | 6/1989 | Lambert | 128/202.16 |
| 4,852,563 A | * | 8/1989 | Gross | 128/202.27 |
| 5,062,420 A | * | 11/1991 | Levine | 128/204.18 |
| 5,184,611 A | * | 2/1993 | Turnbull | 128/207.14 |
| 5,251,617 A | * | 10/1993 | Linder | 128/200.26 |
| 5,309,906 A | | 5/1994 | LaBombard | 128/207.14 |
| 5,315,991 A | * | 5/1994 | Teves | 128/207.14 |
| 5,354,267 A | * | 10/1994 | Niermann et al. | 604/32 |
| 5,404,873 A | * | 4/1995 | Leagre et al. | 128/203.29 |
| 5,694,922 A | * | 12/1997 | Palmer | 128/202.27 |
| 5,713,348 A | * | 2/1998 | Pell | 128/202.27 |
| 5,720,282 A | * | 2/1998 | Wright | 128/203.12 |
| 5,735,271 A | * | 4/1998 | Lorenzen et al. | 128/200.26 |
| 5,787,879 A | * | 8/1998 | Gibson | 128/202.27 |
| 5,855,203 A | * | 1/1999 | Matter | 128/207.14 |
| 6,026,810 A | * | 2/2000 | Baird | 128/202.27 |
| 6,254,589 B1 | * | 7/2001 | Raoz | 128/912 |
| 6,267,754 B1 | * | 7/2001 | Peters | 604/533 |
| 6,273,087 B1 | * | 8/2001 | Boussignac et al. | 128/200.12 |

FOREIGN PATENT DOCUMENTS

| | | | |
|---|---|---|---|
| GB | 2077377 | * | 6/1980 |
| GB | 2192438 | * | 1/1988 |

* cited by examiner

*Primary Examiner*—Aaron J. Lewis
*Assistant Examiner*—Teena Mitchell
(74) *Attorney, Agent, or Firm*—Greenwald & Basch LLP; Howard J. Greenwald

(57) ABSTRACT

A universal respiratory adaptor for connecting medical equipment to a patient respiratory device comprises:

i) a machine end comprises at least two male tapers of different diameters;

ii) a patient end comprises a first female port concentric within a second female port, wherein the second female port has an outer wall which defines a male fitting, and iii) a tubular body portion interconnecting the machine end and the patient end;

wherein the machine end and the body portion comprise a continuous lumen in fluid communication with the first female port.

10 Claims, 4 Drawing Sheets

UNIVERSAL RESPIRATORY DEVICE COUPLER

FIELD OF THE INVENTION

The present invention relates to the field of couplers or adaptors for connecting anaesthesia, ventilator, breathing circuits, resuscitator, medication, or medical treatment devices to other respiratory components including face masks, endotracheal tubes, tracheotomy tubes or their connectors.

BACKGROUND OF THE INVENTION

Breathing devices of various type are routinely used to connect a patient to a respirator or anesthetic delivery machine. The device to be used depends on the mode of communication with the patient's lungs that is desired. For example, this communication may be achieved through the use of a facemask through which the patient breathes or through the use of a tube which is inserted into the trachea. As well as variation in the breathing devices used, there is variation in the anesthesia or respiratory systems used. For example, it is preferable to use smaller diameter tracheal tubes and breathing systems for children. Thus, there is a wide variety in terms of the sizes of the connectors of the various breathing devices and in terms of sizes of the connectors of the various anesthesia and respiratory systems. A real problem is encountered when the connector of a breathing device such as a tracheal tube or face mask is not compatible with the connector of the anesthesia or respiratory system and precious time may be lost trying to find and assemble intermediary connectors.

Various types of adaptors or connectors have been developed to connect a breathing device to a respiratory system. Typically a respirator or anesthesia machine is attached to a Y-piece via inhalation and exhalation tubings. The stem of the Y-piece typically comprises a port to which a tracheal tube connector or facemask can be attached. Various improvements on the basic concept have been attempted. For example, U.S. Pat. No. 4,557,261 describes a connection system for respirator or anesthesia units in which the plug connection is replaced by a system in which disconnection can be effected quickly and easily by actuation of a lever arm on a fastening device.

U.S. Pat. No. 5,735,271 discloses multiple access adaptors for monitoring, sampling, medicating, aspirating and ventilating the respiratory tract of a patient. While a multiplicity of access ports has some advantages, this device does not address the problem of incompatibility between various components of a breathing system.

The optimal respiratory system for an adult might not be optimal for a child or infant. U.S. Pat. No. 4,838,255 discloses a system in which secretions which accumulate in the lungs of an infant or small child can be removed without interrupting the ventilation of the lungs. However, this device does not address the problem of incompatibility between child-oriented and adult-oriented connectors and equipment.

Another type of connector is described in U.S. Pat. No. 5,309,906 which discloses an intubating device or tracheal tubular member for carrying a gas to or from the lungs of the patient which includes an adaptor for interconnecting the tubular member with a source of gas. A compact assembly is provided at the junction of the suction and ventilating hoses so that they are directed to pass over the patient's head, thus removing them from surgical areas that involve the lungs or trachea.

In addition to those described above, many other types of anesthesia and/or respiratory connectors have been designed. However, in spite of the numerous types of adaptors that have been developed, there remains a real and unmet need for a universal connector that facilitates adaption between the exposed fitting of various sized endotracheal tubes and various types of aspirating, respiratory, or anesthesia machines.

SUMMARY OF THE INVENTION

It is an object of an aspect of the present invention to provide a universal adaptor that can facilitate the quick and reliable connection and disconnection of different types of breathing devices to various sizes of respiratory equipment without the need to maintain a large inventory of incompatible parts.

According to one aspect of the invention, there is provided a universal respiratory adaptor comprising:

i) a machine end comprising at least two male tapers of different diameters;

ii) a patient end comprising a first female port concentric within a second female port, wherein said second female port has an outer wall which defines a male fitting; and iii) a tubular body portion interconnecting said machine end and said patient end;

wherein said machine end and said body portion comprise a continuous lumen in fluid communication with said first female port.

BRIEF DESCRIPTION OF THE DRAWINGS

Preferred embodiments of the invention are described with respect to the drawings wherein.

DETAILED DESCRIPTION OF THE PREFERRED EMBODIMENTS

In many situations, it may be necessary to quickly change the apparatus to which a patient's breathing device is connected. For example, it may be desirable to quickly switch from giving a patient oxygen by facemask to giving them anesthetic by tracheal tube. In other cases, it may be desirable to rapidly switch from ventilating the lungs with gases to aspirate secretions or to oxygenate the lungs. These changes must be done reliably and quickly without compromising the safety of the patient.

Further problems may arise when respiratory distress occurs in infants and small children having respiratory problems. This is particularly common in premature infants and newborns. Pediatric and neonatal ventilation has special requirements regarding the size of the tubing to be used (i.e. it should be small and have a low volume). The preferred systems for use in children and in adults typically do not have the same size connectors and thus in an emergency situation, valuable time may be lost trying to connect incompatible systems. For example, when an infant or child is brought to an emergency room in an ambulance, the paramedics may have already inserted an endotracheal tube. If an infant sized endotracheal tube with its associated connector has been inserted and the emergency room only has equipment adapted for connection to an adult sized tracheal tube, intermediary connectors have to be found and quickly attached or else the tracheal tube may have to be replaced. Either way critical time is wasted. On the other hand, if a tracheal tube with an adult sized connector is inserted, this may cause problems if it is determined that the child would be best treated in the neonatal intensive care unit where the respirators and other types of equipment are child-oriented and thus have connections which are incompatible with the adult sized tracheal tube connector.

The present invention addresses these problems by providing a universal respiratory adaptor that can be used to rapidly connect and disconnect incompatible pieces of equipment.

The adaptor 10 has a patient end 12, for connection to a patient device, and a machine end 14 for connection to the tubing of a respirator, anesthetic machine, aspirator or any other medical apparatus that one wants to communicate with the patient device. The patient end 12 is a three-step connector and thus can be connected to at least three different sized breathing devices. The machine end 14 can be connected to at least two different sized ports.

Figure 1:
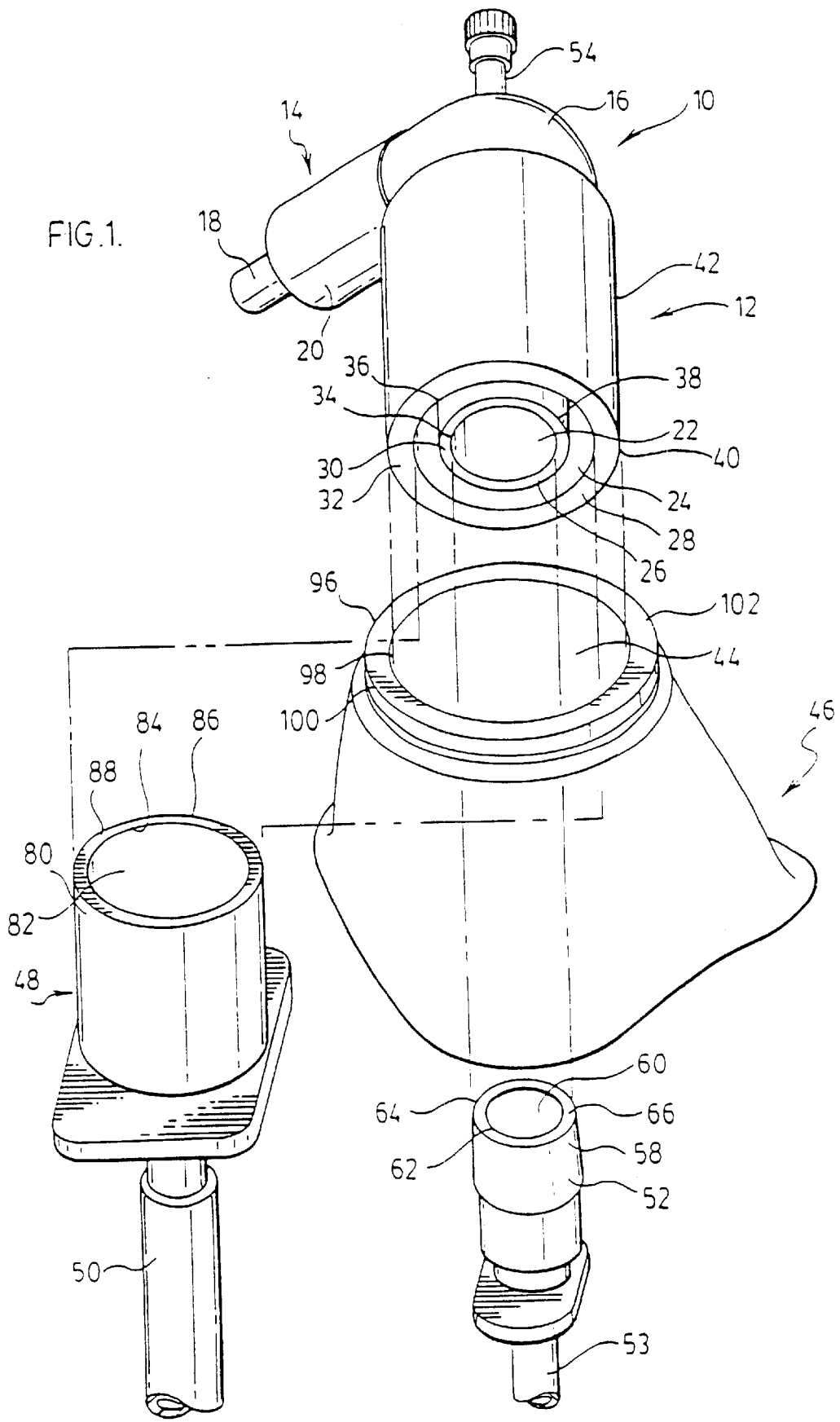
FIG. 1 is a perspective view illustrating various components that may be connected to the patient end of the adaptor of the present invention.
Figure 2:
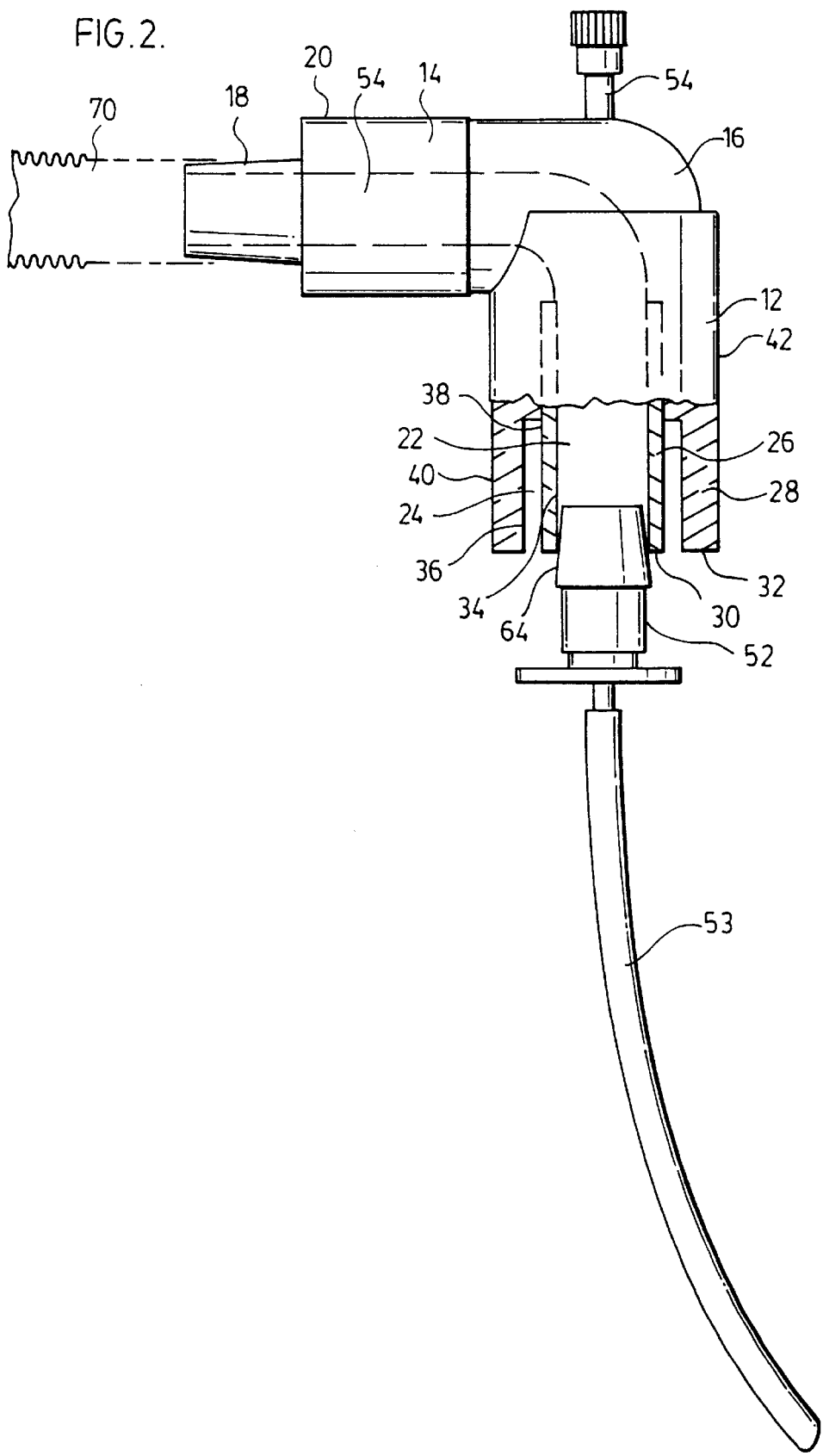
FIG. 2 is a side, partly sectioned, view of the adaptor connected to a child-sized tracheal tube.
Figure 3:
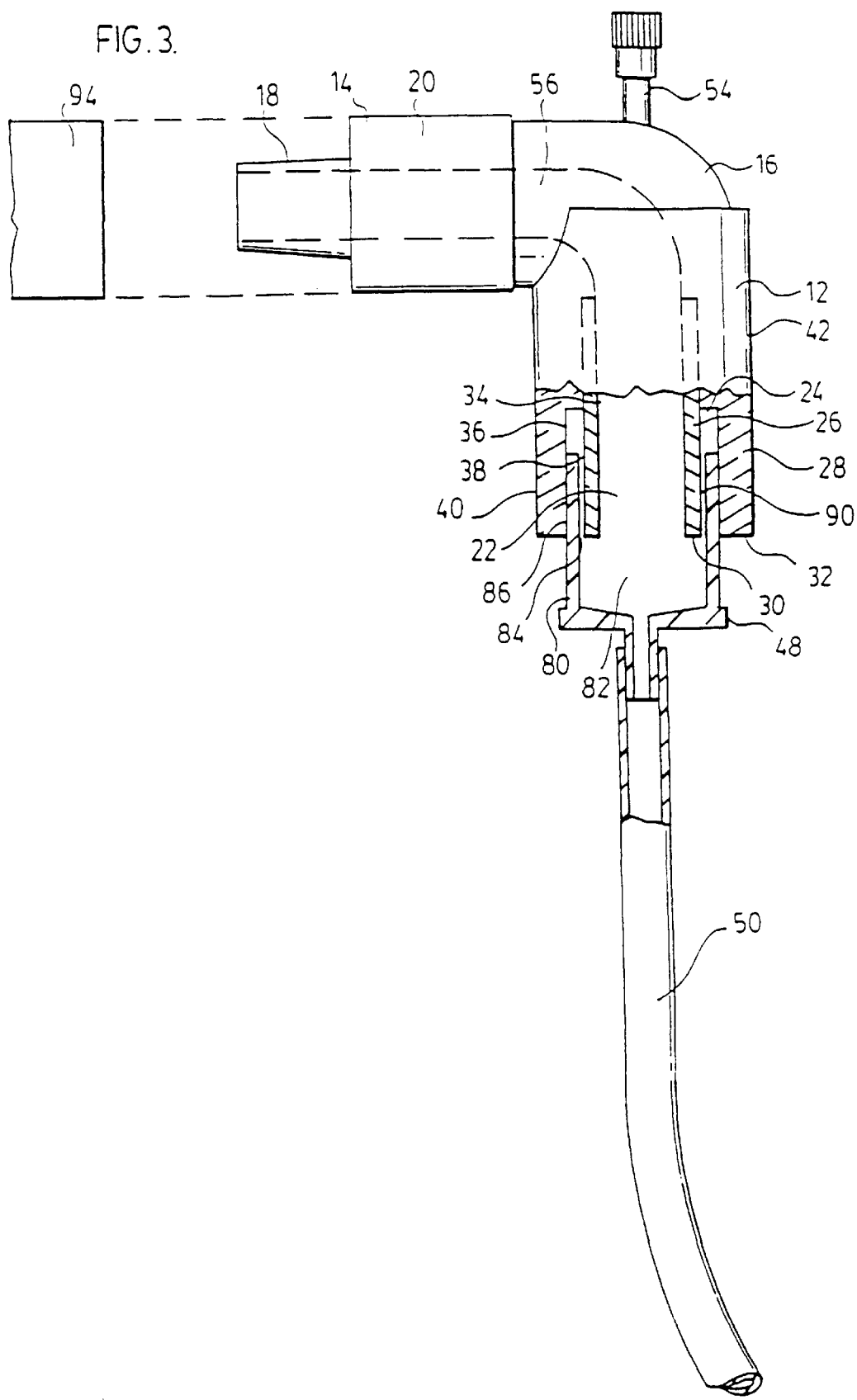
FIG. 3 is a side, partly sectioned, view of the adaptor connected to an adult size tracheal tube.
Figure 4:
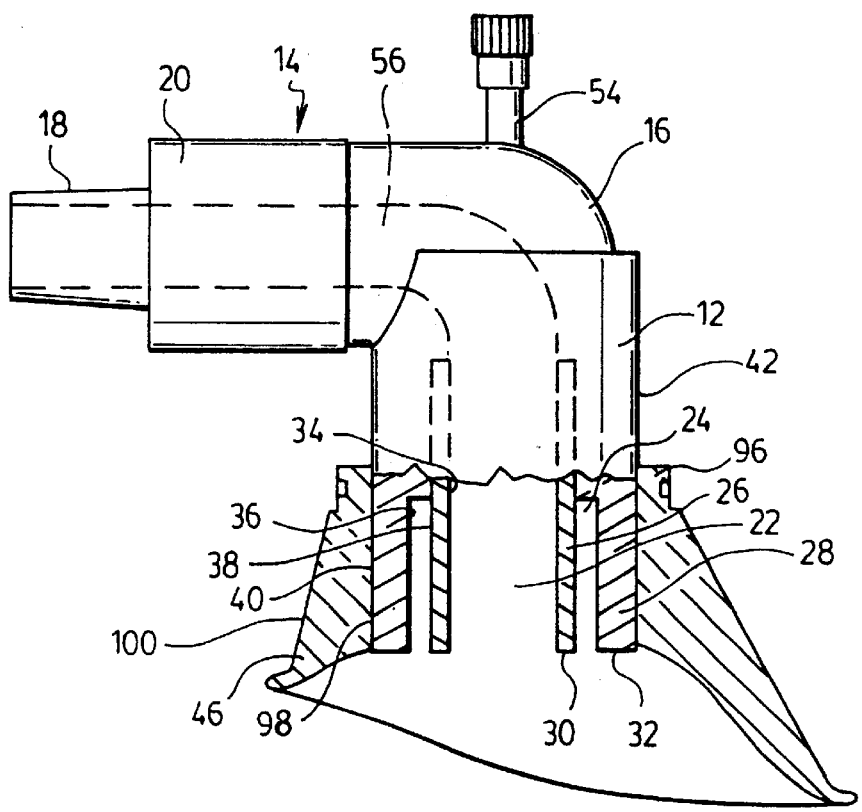
FIG. 4 is a side, partly sectioned view, of the adaptor connected to a facemask.

Referring now to FIG. 1, the potential connection of a variety of patient devices to the adaptor is illustrated. The adaptor 10 comprises a patient end 12 and a machine end 14 for connection to other equipment. A tubular body portion 16 is interposed between the patient end 12 and the machine end 14. The adaptor 10 comprises, at the machine end 14, at least two male tapers. A first male taper 18 is smaller in diameter than a second male taper 20. The patient end 12 has concentric female ports 22, 24. Each of the female ports comprise a circular wall 26, 28, respectively, of uniform thickness which terminates in a blunt leading edge 30, 32, respectively. The circular walls of the female ports 22, 24 have inner wall surfaces 34, 36, respectively and outer wall surfaces 38, 40 respectively. The outer wall 40 of the larger female port 24 acts as a male fitting 42. The male fitting 42 is adapted in size to fit into the female port 44 of a facemask 46. The larger female port 24 is adapted to receive the connector 48 of an adult sized tracheal tube 50 and the smaller female port 22 is adapted to receive the connector 52 of a child sized tracheal tube 53. The adaptor may optionally include a port 54 which can be used for the measurement of respiratory gases. This port 54 may have an internal diameter suitable to admit a suction catheter. The adaptor 10 may also include a fitting for administration of therapeutic materials, such as humidity, nitric oxide or other medications. As shown in FIGS. 2 to 4, the machine end 14 and the body 16 together comprise a continuous lumen 56 which communicates with the female port 22.

In a preferred embodiment, the adaptor 10 comprises, at the machine end 14 for connection to other respiratory equipment, an 8.5 mm. male taper 18 with a lumen at least 6 mm. ID, in series with and adjacent to a 15 mm male taper 20 with a lumen at least 6 mm. ID. The body 16 has a lumen at least 8 mm. ID and may include a gas sample port. This port may admit a 3.3 mm. (10 Fr gauge) [OD 3.3+1−0.15 mm] suction catheter. The body may also carry a conventional 6 to 10 mm. cone connector for supply of gas or vapours, or another connection for supply of medication. Using minimal dead-space, the body 16 connects, at the patient end 12 to a concentric 8.5 mm taper female port 22 within a 15 mm. taper female port 24, where the outer wall 40 of the female port 24 defines a 22 mm. taper male fitting 42. The space between the concentric 22 mm. male and 15 mm. female parts may be solid, or hollow, or supported by several radial fins.

The connection of the small size tracheal tube connector 52 can be seen in FIG. 1 and in more detail in FIG. 2. The connector 52 comprises a circular wall 58 which defines a lumen 60. The circular wall 58 comprises an inner wall surface 62 and an outer wall surface 64 which terminate in a blunt edge 66. The outer wall 64 of connector 52 fits into the female port 22 and 10 engages the inner wall 34 of the port 22 for a press fit connection that is virtually airtight so as not to affect the flow of gases from the port 22 through the lumen 60. In a preferred embodiment the 22, 15 and 8.5 mm dimensions meet the requirements of EN1281.

At the machine end 14, the male taper 20 may be connected, for example, to the connector tubing of a child-adapted respiratory apparatus. Alternatively, it is clearly apparent that the larger male taper 20 could be connected to the larger size connector of an adult respirator thus providing a step up from a small size to a larger size as shown in FIG. 3 (not shown in FIG. 2).

FIGS. 1 and 3 illustrates an adult size tracheal tube connector 48 attached to the adaptor 10. The tracheal connector 48 comprises a circular wall 80 which defines a lumen 82. The circular wall 80 has an inner surface 84 and an outer surface 86 which terminate in a blunt edge 88. The outer surface 84 of the adaptor engages the inner wall 36 of the second female port 24 in a press fit. A space 90 remains between the outer wall 38 of the first female port 22 and the inner surface 84 of the tracheal tube connector 48. In a preferred embodiment, the female port 24 is sized, in accordance with recognized standards to accommodate a 15 mm. male fitting.

The larger male taper 20 at the machine end 14 may be attached to the tubing 94 of an adult-oriented respirator, as illustrated in FIG. 3, or the smaller male taper 18 may be attached to the connector of child adapted equipment to provide a step down. In a preferred embodiment the first male taper 18 is an 8.5 mm. taper and the second male taper 20 is a 15 mm. male taper. It is clearly apparent that other two step tapers, such as 11 mm. and 15 mm. tapers, can also be used depending on the prevalence of particular types of apparatus connectors.

FIGS. 1 and 4 illustrates how a facemask 46 can be attached to the adaptor 10. The face mask comprises a circular wall 96 which defines a female port 44. The circular wall 96 has an inner wall surface 98 and an outer wall surface 100 which terminate in an edge 102. The inner wall 98 of the female port 44 of the facemask 46 engages the outer wall 40 of the second female port 24 which forms the male fitting 42. In a preferred embodiment, the male fitting 42 is a 22 mm. male fitting. The circular wall 28 which defines on its inner surface 36 the female port 24 and on its outer surface 40 the male fitting 42 may be solid, hollow or supported by several radial fins. At the machine end 14, the adaptor 10 can be connected to either child-adapted or adult adapted equipment.

Figure 5A:
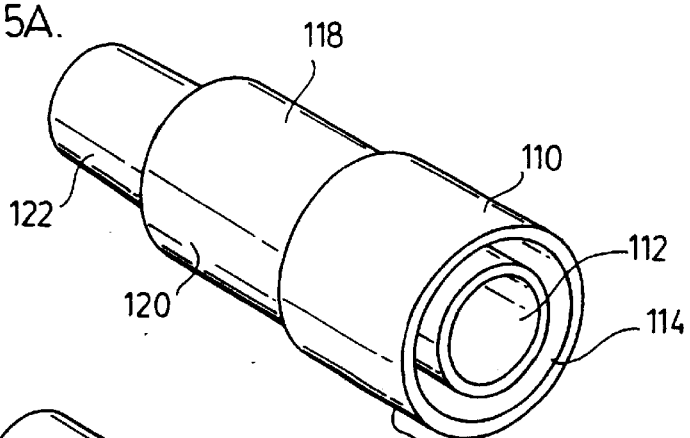
FIG. 5A is a perspective view of an embodiment of the adaptor which is straight.
Figure 5B:
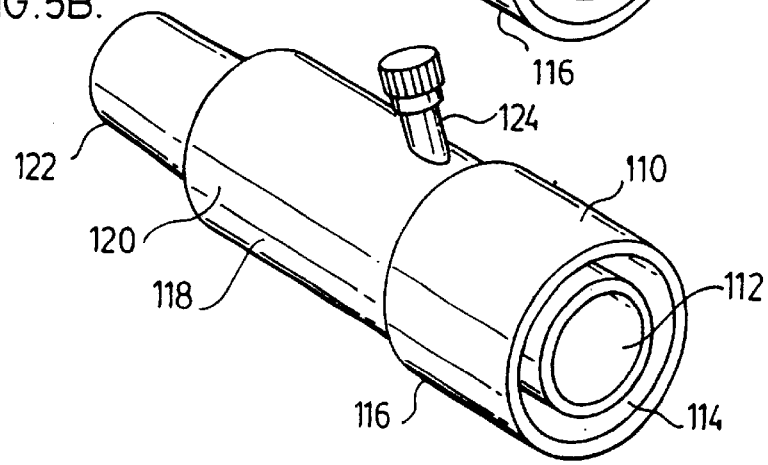
FIG. 5B is a perspective view of an embodiment in which the adaptor is an Ayre's T-piece.

While the adaptor 10 has thus far been illustrated as being essentially L-shaped, it is clearly apparent that the adaptor can also be linear, as illustrated in FIG. 5. The patient end 110 of the adaptor comprises concentric female ports 112, 114 and a male fitting 116. The machine end 118 comprises two male tapers 120, 122. The adaptor may be a straight coupler or it may be a T-connector. When a T-connector is to be used, the machine end 118 including both the small 120 and large male taper 122 should be sufficiently long to engage the connector tubing of the respiratory machine without interference from the T-piece 124.

The adaptor may be manufactured in metal, or plastic material compatible with anaesthetic agents or medications to which it may be exposed and is resistant to deformation, binding or bonding to mating components.

This allows safe and quick change of connections between a patient and a breathing circuit when fittings of different EN Standard sizes are used, articularly between standard child fittings and a breathing circuit of a different standard size. The adaptor may be manufactured to also provide compatibility with other non-EN systems, eg 11 mm systems.

The adaptor of the present invention provides for an easy, secure connection between 8.5 mm taper respiratory system devices commonly used in small children, infants, neonates and premature babies and 1) devices made with a 15 mm taper according to ISO 5356/EN 1281 which is the standard taper for use in large children and adults, and 2) face masks which usually have a 22 mm female port, but may have a 15 mm. male taper.

The rapid connection between components of the '8.5 mm.' and the '15/22 mm' systems is especially important in emergency resuscitation at birth, accidents, cardiac arrest, and in the induction of anaesthesia when it is necessary to rapidly change connections from a face-mask to a tracheal tube connector or tracheostomy tube connector.

When the present adaptor is used, it is not necessary for the anaesthetist to prejudge whether anaesthesia will continue using an 8.5 mm. system, or a 15 mm. system, nor is it necessary to provide a series of intermediary connectors to facilitate the various connections which may be required.

The present invention facilitates interconnection between different interfaces and provides for harmonization between different types of equipment. The adaptor can be used in a variety of different situations. Potential users include, but are not limited to anaesthetists, neonatologists, obstetricians, paediatricians, intensivists/critical care specialists, otolaryngologists, surgeons, respiratory therapists, paramedics, medevac technicians, nurse practitioners, nurses, and other health care professionals.

Although preferred aspects of the invention are described with respect to the drawings, it is understood that variations may be made thereto without departing from the spirit of the invention or the scope of the appended claims.

What is claimed is:

1. A universal respiratory adaptor for connecting medical equipment to a patient respiratory device comprising:
   i) a machine end comprising at least two male tapers of different diameters;
   ii) a patient end comprising a first female port defined by a first circular wall, said first female port being concentric within a second female port defined by a second circular wall, wherein said first female port is adapted in size to receive a pediatric tracheal tube connector, said second female port is adapted to receive an adult tracheal tube connector and said second female port has an outer wall which defines a male fitting adapted to fit into a female port of a facemask, and
   iii) a tubular body portion interconnecting said machine end and said patient end;
   wherein said machine end and said tubular body portion comprise a continuous lumen in fluid communication with said first female port.

2. The adaptor of claim 1 further comprising a sealable port in said tubular body portion.

3. The adaptor of claim 1 wherein one of said at least two male tapers is an 8.5 mm. male taper.

4. The adaptor of claim 1 wherein one of said at least two male tapers is a 15 mm. male taper.

5. The adaptor of claim 1 wherein one of said at least two male tapers is an 11 mm. male taper.

6. The adaptor of claim 1 wherein said first female port is an 8.5 mm. port.

7. The adaptor of claim 1 wherein said second female port is a 15 mm. port.

8. The adaptor of claim 1 wherein said male fitting is a 22 mm. male fitting.

9. The adaptor of claim 1 wherein said machine end and said patient end are essentially at right angles.

10. The adaptor of claim 1 wherein said machine end and said patient end are aligned linearly.

* * * * *